(12) United States Patent
Miller et al.

(10) Patent No.: US 8,927,495 B1
(45) Date of Patent: Jan. 6, 2015

(54) USE OF GNRH AND ANALOGS THEREOF FOR THE PREVENTION AND TREATMENT OF PET FERRET ADRENOCORTICAL HYPERPLASIA

(75) Inventors: Lowell A. Miller, Greeley, CO (US); Robert A. Wagner, Pittsburgh, PA (US)

(73) Assignees: The United States of America as represented by the Secretary of Agriculture, Washington, DC (US); Robert A. Wagner, Pittsburgh, PA (US)

( * ) Notice: Subject to any disclaimer, the term of this patent is extended or adjusted under 35 U.S.C. 154(b) by 0 days.

(21) Appl. No.: 13/479,577

(22) Filed: May 24, 2012

Related U.S. Application Data

(63) Continuation of application No. 12/487,179, filed on Jun. 18, 2009, now abandoned.

(60) Provisional application No. 61/132,651, filed on Jun. 20, 2008.

(51) Int. Cl.
*A61K 38/09* (2006.01)
*A61K 38/10* (2006.01)
*A61K 47/00* (2006.01)
*C07K 7/00* (2006.01)

(52) U.S. Cl.
USPC ........... 514/10.3; 530/300; 530/313; 530/403

(58) Field of Classification Search
None
See application file for complete search history.

(56) References Cited

U.S. PATENT DOCUMENTS

2004/0191266 A1* 9/2004 Miller et al. ............... 424/184.1

OTHER PUBLICATIONS

Wagner et al., AJVR, 2005; 66: 910-914.*

* cited by examiner

*Primary Examiner* — Christina Borgeest
(74) *Attorney, Agent, or Firm* — John Fado; Randall E. Deck; Albert Y. Tsui

(57) ABSTRACT

Adrenocortical disease (ACD) in ferrets develops as a result of the effect of increased concentration of Luteinizing Hormone (LH) on adrenal LH receptors. This increase in LH often results from the neutering of male or female ferrets. Neutered ferrets have no negative feedback of the ovarian or testicular hormone and as a result LH is elevated 3 to 10 times normal. Elevated LH may be prevented and/or treated by injection of GnRH vaccine. Administration of GnRH produces antibodies to endogenous GnRH. The GnRH-anti-GnRH immune-complex is ineffective in stimulating the release of LH and FSH in the anterior pituitary resulting drop in concentration of LH in the systemic circulation. This reduction in LH significantly reduces the occurrence or clinical symptoms of ACD therein. Moreover, treatment of ferrets with the GnRH provides long term relief from ACD for a period of a year or more.

27 Claims, No Drawings

USE OF GNRH AND ANALOGS THEREOF FOR THE PREVENTION AND TREATMENT OF PET FERRET ADRENOCORTICAL HYPERPLASIA

CROSS-REFERENCE TO RELATED APPLICATIONS

This application is a continuation of Ser. No. 12/487,179, filed on Jun. 18, 2009, which claimed the benefit under 35 U.S.C. 1.19(e) of U.S. provisional No. 61/132,651 filed Jun. 20, 2008, the contents of which are hereby incorporated by reference herein in their entirety.

BACKGROUND OF THE INVENTION

1. Field of the Invention

The invention relates to compositions for the control of adrenocortical disease in ferrets.

2. Description of the Prior Art

Adrenocortical disease (ACD) in ferrets (*Mustela putorius furo*) is a common problem in neutered, middle-aged to old ferrets. The adrenal tissues of these ferrets develop nodular hyperplasia, adenomas, or adenocarcinomas which occasionally results in death. The adrenal tissues of these ferrets also exhibit an increase in the production of a variety of steroid hormones, including estradiol, 17-hydroxyprogesterone, and androstenedione, to pathological levels. The major clinical signs attributable to these hormones are alopecia in both sexes and a swollen vulva in females. Pruritus, muscle atrophy, hind limb weakness, and sexual activity or aggression are observed less frequently. Males can develop prostatic cysts, prostatitis, and urethral obstruction. As the disease progresses, there is often a decrease in the apparent quality of life. Occasionally, adrenal gland tumors continue to grow, invade tissues locally, and become necrotic; rarely, they rupture causing death. Additional potentially fatal sequelae include metastases and bone marrow suppression associated with chronic exposure to high serum estrogen concentrations [Rosenthal & Peterson. Evaluation of plasma androgens and estradiol concentrations in ferrets with hyperadrenocorticism. J Am Vet Med Assoc. 1996. 209:1097-1102; Wagner & Dorn. Evaluation of serum estradiol concentrations in alopecic ferrets with adrenal gland tumors. J Am Vet Med Assoc. 1994. 205:703-707; Rosenthal et al. Hyperadrenocorticism associated with adrenocortical tumor or nodular hyperplasia of the adrenal gland in ferrets: 50 cases (1987-1991). J Am Vet Med Assoc. 1993. 203:271-275; and Weiss & Scott. Clinical aspects and surgical treatment of hyperadrenocorticism in the domestic ferret: 94 cases (1994-1996). J Am Anim Hosp Assoc. 1997. 33:487-493].

ACD is thought to be due to an increase LH concentration, often present in neutered ferrets, with acts on the luteinizing hormone (LH) receptors on the adrenocortex resulting in adrenal gland hyperplasia, tumor induction and growth, and increased steroid hormone secretion. There is speculation that the high prevalence of ACD in pet ferrets is associated with neutering at an early age, and may be a result of chronic stimulation of the adrenal gland cortex by pituitary gland gonadotropins (i.e., follicle stimulating hormone [FSH] and LH) (Rosenthal & Peterson. ibid; Shoemaker et al. Correlation between age at neutering and age at onset of hyperadrenocorticism in ferrets. J Am Vet Med Assoc. 2000. 216: 195-197; and Shoemaker et al. The role of luteinizing hormone in the pathogenesis of hyperadrenocorticism in neutered ferrets. Mol and Cell Endocrinol. 2002. 197:117-125). Exposure to abnormally long photoperiods associated with indoor housing of pet ferrets is also thought to contribute to the pathogenesis of ACD. Long light cycles of >8 hours have been shown to stimulate production of gonadotropin-releasing hormone (GnRH) and LH and decrease serum melatonin concentrations, a known antigonadotropic hormone in ferrets [Jallageas et al. Differential photoperiodic control of seasonal variations in pulsatile luteinizing hormone release in long-day (ferret) and short-day (mink) mammals. J Bio Rhythms. 1994. 9(3-4):217-231].

Down regulation of GnRH receptors and subsequent suppression of the production and release of these gonadotropins have been shown to reduce specific hormone production and eliminate hormone effects in ferrets [Wagner et al. Leuprolide acetate treatment of adrenal cortocal disease in ferrets. J Am Vet Med Assoc 2001; 218 (8): 1272-1274; and Wagner et al. Clinical observations and endocrine response to treatment of adrenal cortical disease in ferrets with GnRH (deslorelin acetate) implants. Am J Vet Res 2005; 66 (5): 910-914]. In humans, GnRH analogs administered at pharmacologic doses downregulate GnRH receptors at the pituitary gland.

Gonadotropin-releasing hormone agonists are a relatively new class of drugs, which, when chronically administered, result in marked reductions in blood levels of testosterone and estrogen. These drugs include leuprolide acetate, nafarelin acetate, deslorelin and goserelin acetate. Approved indications for these drugs, depending on the specific agent, include advanced prostate cancer, endometriosis, and precocious puberty. At high doses, GnRH agonists causes downregulation of GnRH receptors at the pituitary gland, thereby inhibiting production and release of gonadotropins (LH and FSH). However, GnRH agonists have a relative short effectiveness and must be delivered in a slow release implant. This implant must be replaced every 12-13 months depending on the mg of drug in the implant.

SUMMARY OF THE INVENTION

We have now discovered that ACD in ferrets, and particularly domestic ferrets, *Mustela putorius* furo, may be prevented and/or treated by administration of gonadotropin releasing hormones (GnRH) or GnRH immunogenic analogs, each conjugated to a carrier protein. Administration of the GnRH or GnRH immunogenic analog significantly reduces the concentration of luteinizing hormone in the serum of a treated ferret, and significantly reduces the occurrence or clinical symptoms of ACD therein. Moreover, treatment of ferrets with the GnRH or GnRH immunogenic analog provides long term relief from ACD for a period of a year or more.

In accordance with this discovery, it is an object of this invention to provide an improved method for reducing the incidence and/or the severity of ACD in ferrets.

It is another object of the invention to provide a method for preventing or controlling ACD in ferrets by reducing the secretion of luteinizing hormone in neutered ferrets.

Yet another object of this invention to provide a method for reducing the incidence and/or the severity of ACD in ferrets for an extended period of time with only a single dose.

Other objects and advantages of this invention will become readily apparent from the ensuing description.

DETAILED DESCRIPTION OF THE INVENTION

It is believed that ACD in ferrets is caused by an increase in the secretion of LH, which acts on the luteinizing hormone (LH) receptors on the adrenocortex and results in adrenal hyperplasia, tumor growth, and increase in steroid hormones such as estradiol, 17-hydroxyprogesterone, androstenedione, and dehydroepiandrosterone. According to this invention, there is provided a method for decreasing the secretion of LH and thereby decreasing the incidence and/or severity of ACD in ferrets, including reducing the above-mentioned adrenal hyperplasia, tumor growth, and steroid hormone production. We have discovered that the administration to ferrets of GnRH or GnRH Immunogenic analogs which are conjugated to a carrier protein, leads to a suppression of the gonadotropins FSH and LH, and eliminates or significantly reduces the clinical signs of ACD. Without wishing to be bound by theory, it is believed that the administration of these immunogenic GnRH or GnRH analogs induces the body to produce antibodies against its own GnRH. These antibodies bind to endogenous GnRH, forming large immune-complexes that travel down the hypophysial stalk. Because of their large size, these immune-complexes are unable to diffuse out of the pituitary stalk capillaries into the pituitary, and without GnRH stimulation of the pituitary, release of LH and FSH is reduced or does not occur, and consequently the stimulation of the adrenal gland cortex and clinical ACD symptoms are also reduced. Moreover, in contrast with treatment with GnRH agonists which provide only temporary relief (3 to 6 months) of ACD, treatment with GnRH or GnRH analog vaccines in accordance with the instant invention provides significantly longer control of ACD, with a single dose administration providing effective reduction in LH serum concentrations and ACD symptoms for a period of a year or more.

GnRH (also known as Luteinizing Hormone Releasing Hormone, or "LHRH") has long been recognized as being of central importance to the regulation of fertility in. animals. GnRH is a decapeptide which has the same amino acid sequence, i.e., pGlu-His-Trp-Ser-Tyr-Gly-Leu-Arg-Pro-GlyNH$_2$ (SEQ. ID NO. 1) in all mammals. Throughout this description, the amino acid sequences conform with conventional practice with the amino terminal amino acid on the left and the carboxy terminal amino acid to the right. Owing to its small size, GnRH and its analogs are relatively poorly capable of stimulating the immune system to produce antibodies. To render these compounds immunogenic, they are generally conjugated to an immunogenic carrier in such manner that the resultant immunogen is capable of stimulating the immune system of the ferret to produce antibodies capable of binding to unconjugated GnRH.

While GnRH may be used in the immunogen preparation and is generally preferred, a variety of GnRH immunogenic analogs have also been described which are suitable for use herein. As noted hereinabove, GnRH is a small decapeptide. As defined herein, immunogenic analogs of GnRH include compounds containing a substitution, deletion, or insertion of between one and five amino acid residues in the above-mentioned GnRH amino acid sequence, as well as dimers or polymers thereof, which compound retains the ability to induce or stimulate the production in a subject animal of antibodies which bind (i.e., cross-react) to GnRH. The GnRH analog will preferably retain at least five consecutive amino acids from the GnRH decapeptide. The substitutions and insertions can be accomplished with natural or non-natural amino acids, and substitutions are preferably conservative substitutions made with amino acids which maintain substantially the same charge and hydrophobicity as the original amino acid. Moreover, the analog may itself be immunogenic or it may be coupled to an immunogenic carrier such as described hereinbelow.

GnRH or GnRH immunogenic analogs or mimics which are suitable for use herein have also been previously described for the immunocontraception of animals by Miller (U.S. patent application Ser. No. 10/833,903, now published as publication no. 2004/0191266, the contents of which are incorporated by reference herein). Suitable immunogenic analogs of GnRH have also been described, for example, in Meleon (U.S. Pat. Nos. 5,484,592 and 6,284,733), Mia (U.S. Pat. No. 4,608,251), Ladd et al. (U.S. Pat. No. 5,759,551), Hoskinson et al. (published PCT application WO8805308), and Russell-Jones et al. (U.S. Pat. No. 5,403,586) the contents of each of which are incorporated by reference herein. Thus, suitable GnRH analogs include but are not limited to GnRH peptides wherein the Gly at position 6 of the GnRH decapeptide has been replaced by a dextrorotary (D)-amino acid such as D-trp, D-glu, or D-lys (SEQ. ID NO. 2, 3, and 4, respectively); GnRH peptides wherein the p-Glu at position 1 of the GnRH decapeptide has been replaced by a Glu, His, or Pro (SEQ. ID NO. 5, 6, and 7, respectively); any continuous 5, 6, 7, 8, or 9 amino acid fragment of the GnRH decapeptide, such as pGlu-His-Trp-Ser-Tyr, pGlu-His-Trp-Ser-Tyr-Gly, pGlu-His-Trp-Ser-Tyr-Gly-Leu, His-Trp-Ser-Tyr-Gly-Leu-Arg, Trp-Ser-Tyr-Gly-Leu-Arg, Ser-Tyr-Gly-Leu-Arg-Pro-Gly-NH$_2$, and Tyr-Gly-Leu-Arg-Pro-Gly-NH$_2$ (SEQ. ID NOS. 9-15, respectively); naturally occurring chicken GnRH II, pGlu-His-Trp-Ser-His-Gly-Trp-Tyr-Pro-Gly-NH$_2$ (SEQ. ID NO. 16); naturally occurring salmon GnRH, pGlu-His-Trp-Ser-Tyr-Gly-Trp-Leu-Pro-Gly-NH$_2$ (SEQ. ID NO. 17); the nona- or decapeptide (Cys)-Lys-Trp-Ser-Tyr-Gly-Leu-Arg-Pro-Gly-NH$_2$, wherein the amino terminal Cys is optional (SEQ. ID NOS. 18 and 19, respectively) or a dimer of the decapeptide wherein the amino terminal Cys are coupled to one another (SEQ. ID NO. 20); a polymer of two or more decapeptides in tandem of the formula Z$^1$-Glx-His-Trp-Ser-Tyr-Gly-Leu-Arg-Pro[-Gly-X-Gln-His-Trp-Ser-Tyr-Gly-Leu-Arg-Pro]$_n$-Gly-Z$^2$ wherein n is an integer greater than or equal to 1, X is a direct bond or a spacer, Z$^1$-Glx is pGlu or Gln having an amino acid tail attached thereto for coupling to a carrier protein, and Gly-Z$^2$ is Gly-NH$_2$ or Gly having an amino acid tail attached thereto for coupling to a carrier protein (SEQ. ID NO. 21); and a peptide having the sequence pGlu-His-Trp-Ser-Tyr-Y-Leu-Arg-Pro-Gly-Gln-His-Trp-Ser-Tyr-Y-Leu-Arg-Pro-Gly-Cys wherein Y is independently Gly or a D-amino acid which may optionally contain an amino acid side chain attached thereto for coupling to a carrier protein (SEQ. ID NO. 22) or a dimer thereof.

Although the GnRH may be isolated from natural sources, for practical purposes GnRH or and its analogs may be synthesized by a variety of conventional methods Such techniques include but are not limited to methods well known to those skilled in the art of peptide synthesis, e.g., solution phase synthesis [see Finn and Hoffman. In "Proteins," Vol. 2, 3rd Ed., H. Neurath and R. L. Hill (eds.), Academic Press. New York. pp. 105-253 (1976)), or solid phase synthesis (see Barany and Merrifield. In "The Peptides" Vol. 2. E. Gross and J. Meienhofer (eds.). Academic Press. New York. pp. 3-284 (1979)], or stepwise solid phase synthesis as reported by Merrifield [J. Am. Chem. Soc. 1963. 85: 2149-2154], the contents of each of which are incorporated herein by reference.

Conjugation of the GnRH or its analog to an immunogenic carrier in order to increase the immune response to the peptide may be conducted using previously described techniques, and a plurality carriers and carrier coupling techniques have been previously described for GnRH or its analogs. See for example, Meleon, Mia, Ladd et al., Hoskinson et al., and Russell-Jones et al. mentioned above. However, in a preferred embodiment, GnRH or an analog thereof is conjugated to immunogenic mollusk hemocyanin carrier protein, directly or indirectly through the C-terminal end of the GnRH or analog. Suitable immunogenic mollusk hemocyanin proteins include *Concholepas concholepas* hemocyanin protein, Keyhole Limpet (*Megathura crenulate*) hemocyanin protein (KLH), Horseshoe crab (*Limulus polyphemus*) hemocyanin protein, and Abalone (*Haliotis tuberculata*) hemocyanin protein, with KLH and *Concholepas concholepas* hemocyanin protein being preferred.

Conjugation of GnRH or its analog to the mollusk hemocyanin protein is preferably conducted using a cross-linking agent to allow a large number of GnRH or analog molecules (i.e., 200 or more) to be coupled to a single carrier protein molecule, effectively covering its outer surface with consistently aligned epitopes of the GnRH displaying the same basic conformation. To ensure this consistent alignment, the GnRH (or its analog) is coupled through its C-terminal end to the N-terminal end of the carrier protein through a bifunctional cross-linking agent. In a particularly preferred embodiment, the GnRH/carrier conjugate may be shown by the formula:

$$(X-A_m-B-L)_n-R \qquad (I)$$

wherein X is GnRH or a GnRH immunogenic analog, A is an optional amino acid spacer such as Gly, m is an integer greater than or equal to 0, B is an amino mercaptan, R is an intact immunogenic mollusk hemocyanin protein, L is a bifunctional crosslinking agent effective for simultaneously binding to the thiol of the mercaptan and to free amine moieties of the immunogenic mollusk hemocyanin protein, and n is an integer greater than or equal to about 200. A variety of amino mercaptans may be used, provided that it possesses a free amino moiety for binding to the C-terminal end of X (or A if present) and a free thiol moiety for binding to the bifunctional crosslinking agent, although cysteine is preferred. Preferred bifunctional crosslinking agents include succinimidyl-4-(N-maleimidomethyl)cyclohexane-1-carboxylate (SMCC) or sulfo-SMCC (s-SMCC), either of which form a maleimide-activated carrier protein. Other crosslinking agents suitable for conjugating the carrier protein and GnRH through the thiol group of the amino mercaptan include but are not limited to the organic solvent soluble agents Succinimidyl 4-(p-maleimidophenyl)-butyrate (SMPB), -[(γ-Maleimidobutyryl)oxy]succinimide ester (GMBS), -Succinimidyl[4-iodoacetyl]-aminobenzoate (SIAB), and m-Maleimidobenzyl-N-hydroxysuccinimide ester (MBS), or their corresponding water soluble sulfonated forms sulfo-SMPB (s-SMPB), sulfo-GMBS (sGMBS), sulfo-SIAB (s-SIAB), and sulfo-MBS (s-MBS).

Preparation of the above-mentioned GnRH/mollusk hemocyanin protein conjugate is preferably conducted under conditions of approximately neutral pH and high salt concentrations to prevent the disassociation of the protein into subunits, and thereby prevent mollusk protein epitopes from being exposed to the ferret's immune system. Thus, the protein is preferably dissolved in a buffer having an NaCl concentration greater than or equal to about 0.6 M, particularly about 0.9 M. Addition of sucrose to the carrier protein solution is also preferred to reduce the denaturation of the protein during freeze lyophilization processing and to allow the material to be rehydrated without precipitation. A detailed description of the conjugation procedure is provided in Example 2 of the above-mentioned published U.S. application no. 2004/0191266.

Treatment of a subject ferret with the carrier protein-conjugated GnRH or GnRH Immunogenic analogs is preferably initiated as soon as possible after diagnosis of ACD. Diagnosis is generally determined after the recognition of one or more clinical symptoms associated with this disease. Such symptoms include, but are not limited to one or more of adrenal hyperplasia, tumor growth, and significantly elevated levels of steroid hormones such as estradiol, 17-hydroxyprogesterone, androstenedione, and dehydroepiandrosterone. In an alternative preferred embodiment, the compound may be administered prophylactically to a ferret prior to development of clinical symptoms of ACD. Such prophylactic treatment may be initiated at any time or age after the ferret attains immunocompetence, which is normally after about 2 months of age. However, because neutered ferrets are particularly susceptible to development of ACD, the treatment of ferrets which have been neutered, or are to be neutered, is preferred.

The carrier protein-conjugated GnRH or GnRH Immunogenic analogs may be administered to the subject animal by parenteral injection (e.g., subcutaneous, intravenous, or intramuscular). Treatment of ferrets with the carrier protein-conjugated GnRH or GnRH Immunogenic analogs provides effective reduction in LH secretion and control of ACD in ferrets for periods of approximately a year or more after only a single dose or shot. Thus, a preferred dosage regimen comprises administration of a single dose per year, and may be continued for as long as desired, preferably for the life of the ferret. However, as a practical matter, it is recognized that treatment programs utilizing two or more doses per year may exhibit an even greater decrease in LH secretion and greater ACD control, and may therefore also be utilized. The method of this invention is effective for the treatment of both male and female ferrets.

The carrier protein-conjugated GnRH or GnRH Immunogenic analogs are prepared for administration by formulation in an effective amount or dosage with a pharmaceutically acceptable carrier or diluent, such as physiological saline, mineral oil, vegetable oils, aqueous carboxymethyl cellulose or polyvinylpyrrolidone, with physiological saline being preferred. However, when using compositions which include a mollusk hemocyanin carrier protein, the vaccine composition will preferably further include physiologically buffered saline with a high salt concentration to prevent dissociation of the protein. The salt (NaCl) concentration of the vaccine composition is preferably greater than or equal to about 0.7 M and less than or equal to about 1.0 M, and the pH of said vaccine composition is between about 7.0 and 8.0, with 7.4 being preferred. Appropriate adjuvants as known in the art may also be included in the formulation. Without being limited thereto, suitable adjuvants include but are not limited to mineral oil, vegetable oils, alum, Freund's incomplete adjuvant, Freund's incomplete adjuvant, and preferably the *Mycobacterium avium* subspecies *avium* in mineral oil adjuvant of Miller (U.S. patent application Ser. No. 10/833,903, now published as publication no. 2004/0191266, the contents of which are incorporated by reference herein). Other known immunogenic agents used in conventional vaccines for ferrets may also be included in the formulation.

The immunogenic GnRH or GnRH analogs are administered in an amount effective to reduce the secretion of LH by a subject ferret. As noted hereinabove, the administration of the immunogenic GnRH or GnRH analogs induces the ferret to produce antibodies against its own GnRH, which antibodies bind to endogenous GnRH, reducing or preventing GnRH stimulation of the pituitary, consequently reducing the release of LH (as well as FSH) which ultimately leads to the development of ACD. Thus, as used herein, an "effective amount" of the immunogenic carrier protein-conjugated GnRH or GnRH analogs is preferably defined as that amount which will induce antibodies against GnRH and thereby significantly reduce the release or secretion of LH in a treated ferret in comparison to untreated ferrets. A reduction of LH may be demonstrated by a significant reduction in the serum concentration of LH in treated ferrets in comparison with untreated control ferrets. While LH may be measured directly, in a preferred embodiment a decrease in LH is most readily determined qualitatively by measuring a decrease in serum steroid hormone levels, particularly androgens such as testosterone in males or progesterone in females. Moreover, because the development of ACD is due to this increase in LH secretion, it is also understood that a reduction in the secretion of LH may be evidenced by a significant reduction in one or more of the above-mentioned symptoms of ACD, as a reduction in alopecia, pruritus, swollen vulvas in females, sexual and aggressive behaviors, and possibly a reduction or slowing of adrenal hyperplasia and tumor growth in treated ferrets in comparison to untreated ferrets. Accordingly, the GnRH or GnRH analog conjugate may be administered in an amount effective to induce one or more of these responses as determined by routine testing. The actual effective amount will of course vary with the specific GnRH or GnRH analog, the immunogenic carrier and manner of conjugation, and the treatment regimen (i.e., treatment with only a single dose per year, or treatment with multiple doses per year), and may be readily determined empirically by the practitioner skilled in the art using an antigen dose response assay. For example, without being limited thereto, it is envisioned that suitable single shot doses of the GnRH or GnRH analog conjugate for the treatment of ferrets may be between about 200 μg and about 1800 μg per ferret, preferably between about 200 μg and about 800 μg, and most preferably about 500 μg The doses presented above are provided only as a guide for ferrets treated approximately yearly. For treatment programs utilizing two doses per year, it is envisioned that the doses described above for a single dose regimen could be cut in half for each dose.

The following examples are intended only to further illustrate the invention and are not intended to limit the scope of the invention which is defined by the claims.

Example 1

Materials and Methods

Eight pet ferrets with ACD of varying severity and duration (2 months) were vaccinated intramuscular (IM) with 0.5 ml (500 μg) of GnRH-KLH conjugate, formulated with the *Mycobacterium avium* subspecies *avium* in mineral oil adjuvant, prepared as described by Miller (Examples 1 and 2 of U.S. patent application Ser. No. 10/833,903, now published as publication no. 2004/0191266, the contents of which are incorporated by reference herein). As noted above, GnRH may be conjugated to several mollusk proteins but preferably KLH or blue mollusk protein. Before vaccination and at 2 and 3 months post vaccination, blood was collected for plasma hormone analyses and GnRH antibody concentrations.

The diagnosis of ACD was confirmed in the ferrets on the basis of clinical findings and results of a plasma hormone profile. Clinical findings included alopecia, pruritus, swollen vulva in females, and increased sexual behaviors and aggression. A subjective assessment of the severity of clinical signs at the start of the investigation (and later in response to vaccine treatment) were performed by comparing each ferret with a clinically normal ferret. Severity of alopecia (loss of hair) was estimated (100% representing full normal pelage and 0% representing whole body alopecia). Pruritus, vulvar size, sexual behavior, and aggression were evaluated as normal, decreased, no change, or increased.

Clinical response to vaccination was monitored via a physical examination performed monthly. At each examination, clinical evaluations and scoring of the severity of clinical signs in affected animals were performed.

Plasma samples obtained before treatment and at 2 and 3 months after treatment were analyzed for estradiol, androstenedione, and 17-hydroxyprogesterone concentrations. Reference ranges for hormones are as follows: estradiol, 30 to 180 pmol/L; androstenedione, 1 to 15 nmol/L; and 17-hydroxyprogesterone, 0.05 to 0.8 nmol/L (Rosenthal & Peterson. Evaluation of plasma androgens and estradiol concentrations in ferrets with hyperadrenocorticism. J Am Vet Med Assoc. 1996. 209:1097-1102; and Wagner & Dorn. Evaluation of serum estradiol concentrations in alopecic ferrets with adrenal gland tumors. J Am Vet Med Assoc. 1994. 205:703-707).

TABLE 1

0.5 ml IM Ferret GnRH Vaccination ACD Tx Study:

| 30-180 pmol/L Pre-GnRH Estradiol | 0-15 nmol/L Andro | 0-0.8 nmol/L 17OH Prog |
|---|---|---|
| 196.00 | 75.40 | 5.00 |
| 190.00 | 204.20 | 7.60 |
| 382.00 | 190.20 | 6.00 |
| 128 | 0.88 | 22.7 |
| 302.00 | 20.60 | 2.67 |
| 80 | 27.9 | 2.73 |
| 202.5 | 29 | 0.27 |
| 171.00 | 72.90 | 2.40 |
| 220.00 | 77.80 | 19.00 |

| 2 mos Post Estradiol | Andro | 17OH Prog | Response 2 mo Post | Response >2 mo | GnRH titer @ 2 mo |
|---|---|---|---|---|---|
| 79.00 | 9.40 | 0.20 | 100% | 100% | 128,000 |
| 131.00 | 3.80 | 0.27 | 80% | 90% | 32,000 |
| 129.00 | 9.10 | 0.12 | 100% | 100% | 128,000 |
| 93.00 | 9.10 | 0.30 | 100% | 100% | 128,000 |
| 135.00 | 2.10 | 0.15 | 80% | 100% | 32,000 |
| 79.00 | 2.40 | 0.20 | 20% | 80% | 8,000 |
| 85.3 | 11.2 | 0.88 | 40% | 60% | 32,000 |
| 120 | 3.5 | 0.12 | 100% | 100% | 128,000 |
| 190.00 | 6.30 | 1.61 | 0% | 0% | ND |

ND = non- detectable

Discussion of Results:

Vaccination with GnRH-KLH or GnRH-Blue protein resulted in a significant antibody titer against GnRH which in turn significantly dropped the androsterone and 17-OH progesterone concentration. A drop in both of these steroids reflected a drop in LH. The drop in LH was also reflected in the improvement of the clinical condition of the neutered ferret. The main clinical improvement was the regrowth of hair in the early stages of the disease. The drop in estradiol was not as dramatic as in the 17-OH progesterone and androsterone. This was probably due to the fact the GnRH does not suppress FSH as much as the LH.

We claim:

1. A method for reducing the incidence of or treating adrenocortical disease in domestic ferrets, *Mustela putorius furo*, comprising administering a composition comprising gonadotropin-releasing hormone (GnRH) conjugated to a carrier protein or a GnRH immunogenic analog conjugated to a carrier protein, to said ferret in an amount effective to stimulate an immune response in said ferret to produce antibodies to endogenous GnRH and thereby significantly reduce the concentration of luteinizing hormone in the serum of said ferret, wherein said amount of said GnRH conjugated to a carrier protein or a GnRH immunogenic analog conjugated to a carrier protein administered is 500 μg per ferret.

2. The method of claim 1 wherein said ferrets are neutered.

3. The method of claim 1 wherein said ferrets are neutered males.

4. The method of claim 1 wherein said ferrets are neutered females.

5. The method of claim 1 wherein said composition is further effective to significantly reduce the concentration of follicle stimulating hormone in the serum of said ferret.

6. The method of claim 1 wherein said GnRH or a GnRH immunogenic analog comprises mammalian GnRH or a mammalian GnRH immunogenic analog.

7. The method of claim 1 wherein said carrier protein is Keyhole Limpet hemocyanin carrier protein or blue protein mollusk protein, and wherein said GnRH or GnRH immunogenic analog is conjugated to said carrier protein through the C-terminal end of said GnRH or GnRH immunogenic analog.

8. The method of claim 1 wherein said composition is administered in a single shot.

9. The method of claim 1 wherein said composition is administered approximately one or two times per year.

10. The method of claim 1 wherein said composition is administered to said ferrets at about 2 months of age and older.

11. The method of claim 10 wherein said adjuvant comprises mineral oil and killed cells of *Mycobacterium avium* subspecies *avium*, the concentration of said killed cells of *Mycobacterium avium* being greater than or equal to about 50 ug per ml and less than or equal to about 400 ug per ml, measured as the dry weight of said killed cells per ml of said composition.

12. The method of claim 1 wherein said composition further comprises an adjuvant effective to enhance the immune response in said ferret to said GnRH or GnRH immunogenic analog.

13. The method of claim 1 wherein said composition comprises mammalian GnRH conjugated to a carrier protein.

14. A method for vaccination of domestic ferrets, *Mustela putorius* furo, to reduce the incidence of adrenocortical disease therein, comprising administering a composition comprising gonadotropin-releasing hormone (GnRH) conjugated to a carrier protein or a GnRH immunogenic analog conjugated to a carrier protein to said ferret, prior to development of clinical symptoms of adrenocortical disease, in an amount effective to stimulate an immune response in said ferret to produce antibodies to endogenous GnRH and thereby significantly reduce the concentration of luteinizing hormone in the serum of said ferret.

15. The method of claim 14 wherein said ferrets are neutered.

16. The method of claim 14 wherein said ferrets are neutered males.

17. The method of claim 14 wherein said ferrets are neutered females.

18. The method of claim 14 wherein said composition is further effective to significantly reduce the concentration of follicle stimulating hormone in the serum of said ferret.

19. The method of claim 14 wherein said GnRH or a GnRH immunogenic analog comprises mammalian GnRH or a mammalian GnRH immunogenic analog.

20. The method of claim 14 wherein said carrier protein is Keyhole Limpet hemocyanin carrier protein or blue protein mollusk protein, and wherein said GnRH or GnRH immunogenic analog is conjugated to said carrier protein through the C-terminal end of said GnRH or GnRH immunogenic analog.

21. The method of claim 14 wherein
said amount of said GnRH conjugated to a carrier protein or a GnRH immunogenic analog conjugated to a carrier protein administered is between 200 μg and 1800 μg per ferret.

22. The method of claim 21 wherein said composition is administered approximately one or two times per year.

23. The method of claim 14 wherein said composition is administered in a single shot.

24. The method of claim 14 wherein said composition is administered to said ferrets about 2 months of age and older.

25. The method of claim 14 wherein said composition further comprises an adjuvant effective to enhance the immune response in said ferret to said GnRH or GnRH immunogenic analog.

26. The method of claim 25 wherein said adjuvant comprises mineral oil and killed cells of *Mycobacterium avium* subspecies *avium*, the concentration of said killed cells of *Mycobacterium avium* being greater than or equal to 50 ug per ml and less than or equal to 400 ug per ml, measured as the dry weight of said killed cells per ml of said composition.

27. The method of claim 14 wherein said composition comprises mammalian GnRH conjugated to a carrier protein.

\* \* \* \* \*

SEQUENCE LISTING

<160> NUMBER OF SEQ ID NOS: 21

<210> SEQ ID NO 1
<211> LENGTH: 10
<212> TYPE: PRT
<213> ORGANISM: Artificial
<220> FEATURE:
<223> OTHER INFORMATION: A synthesized peptide having the same amino
      acid sequence of GnRH common to all mammals
<220> FEATURE:
<221> NAME/KEY: misc_feature
<222> LOCATION: (1)..(1)
<223> OTHER INFORMATION: Xaa can be any naturally occurring amino acid

<400> SEQUENCE: 1

Xaa His Trp Ser Tyr Gly Leu Arg Pro Gly
1               5                   10

<210> SEQ ID NO 2
<211> LENGTH: 10
<212> TYPE: PRT
<213> ORGANISM: Artificial
<220> FEATURE:
<223> OTHER INFORMATION: a GnRH analog wherein the Gly at position 6 is
      replaced with D-trp
<220> FEATURE:
<221> NAME/KEY: misc_feature
<222> LOCATION: (1)..(1)
<223> OTHER INFORMATION: Xaa can be any naturally occurring amino acid

<400> SEQUENCE: 2

Xaa His Trp Ser Tyr Trp Leu Arg Pro Gly
1               5                   10

<210> SEQ ID NO 3
<211> LENGTH: 10
<212> TYPE: PRT
<213> ORGANISM: Artificial
<220> FEATURE:
<223> OTHER INFORMATION: A GnRH analog wherein the Gly at position 6 is
      replaced with D-glu
<220> FEATURE:
<221> NAME/KEY: misc_feature
<222> LOCATION: (1)..(1)
<223> OTHER INFORMATION: Xaa can be any naturally occurring amino acid

<400> SEQUENCE: 3

Xaa His Trp Ser Tyr Glu Leu Arg Pro Gly
1               5                   10

<210> SEQ ID NO 4
<211> LENGTH: 10
<212> TYPE: PRT
<213> ORGANISM: Artificial
<220> FEATURE:
<223> OTHER INFORMATION: A GnRH analog wherein the Gly at position 6 is
      replaced with D-lys
<220> FEATURE:
<221> NAME/KEY: misc_feature
<222> LOCATION: (1)..(1)
<223> OTHER INFORMATION: Xaa can be any naturally occurring amino acid

<400> SEQUENCE: 4

Xaa His Trp Ser Tyr Lys Leu Arg Pro Gly
1               5                   10

<210> SEQ ID NO 5
<211> LENGTH: 10
<212> TYPE: PRT
<213> ORGANISM: Artificial

```
<220> FEATURE:
<223> OTHER INFORMATION: A GnRH analog wherein the p-Glu at position 1
      is replaced with Glu

<400> SEQUENCE: 5

Glu His Trp Ser Tyr Gly Leu Arg Pro Gly
1               5                   10

<210> SEQ ID NO 6
<211> LENGTH: 10
<212> TYPE: PRT
<213> ORGANISM: Artificial
<220> FEATURE:
<223> OTHER INFORMATION: A GnRH analog wherein the p-Glu at position 1
      is replaced with His

<400> SEQUENCE: 6

His His Trp Ser Tyr Gly Leu Arg Pro Gly
1               5                   10

<210> SEQ ID NO 7
<211> LENGTH: 10
<212> TYPE: PRT
<213> ORGANISM: Artificial
<220> FEATURE:
<223> OTHER INFORMATION: A GnRH analog wherein the p-Glu at position 1
      is replaced with Pro

<400> SEQUENCE: 7

Pro His Trp Ser Tyr Gly Leu Arg Pro Gly
1               5                   10

<210> SEQ ID NO 8
<211> LENGTH: 5
<212> TYPE: PRT
<213> ORGANISM: Artificial
<220> FEATURE:
<223> OTHER INFORMATION: A continuous 5 amino acid fragment of the GnRH
      peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 8

Xaa His Trp Ser Tyr
1               5

<210> SEQ ID NO 9
<211> LENGTH: 6
<212> TYPE: PRT
<213> ORGANISM: Artificial
<220> FEATURE:
<223> OTHER INFORMATION: A continuous 6 amino acid fragment of the GnRH
      peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 9

Xaa His Trp Ser Tyr Gly
1               5

<210> SEQ ID NO 10
<211> LENGTH: 7
<212> TYPE: PRT
<213> ORGANISM: Artificial
<220> FEATURE:
```

```
<223> OTHER INFORMATION: A continuous 7 amino acid fragment of the GnRH
      peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 10

Xaa His Trp Ser Tyr Gly Leu
1               5

<210> SEQ ID NO 11
<211> LENGTH: 7
<212> TYPE: PRT
<213> ORGANISM: Artificial
<220> FEATURE:
<223> OTHER INFORMATION: A continuous 7 amino acid fragment of the GnRH
      peptide

<400> SEQUENCE: 11

His Trp Ser Tyr Gly Leu Arg
1               5

<210> SEQ ID NO 12
<211> LENGTH: 6
<212> TYPE: PRT
<213> ORGANISM: Artificial
<220> FEATURE:
<223> OTHER INFORMATION: A continuous 6 amino acid fragment of the GnRH
      peptide

<400> SEQUENCE: 12

Trp Ser Tyr Gly Leu Arg
1               5

<210> SEQ ID NO 13
<211> LENGTH: 7
<212> TYPE: PRT
<213> ORGANISM: Artificial
<220> FEATURE:
<223> OTHER INFORMATION: A continuous 7 amino acid fragment of the GnRH
      peptide

<400> SEQUENCE: 13

Ser Tyr Gly Leu Arg Pro Gly
1               5

<210> SEQ ID NO 14
<211> LENGTH: 6
<212> TYPE: PRT
<213> ORGANISM: Artificial
<220> FEATURE:
<223> OTHER INFORMATION: A continuous 6 amino acid fragment of the GnRH
      peptide

<400> SEQUENCE: 14

Tyr Gly Leu Arg Pro Gly
1               5

<210> SEQ ID NO 15
<211> LENGTH: 10
<212> TYPE: PRT
<213> ORGANISM: Gallus gallus
<220> FEATURE:
<221> NAME/KEY: misc_feature
<222> LOCATION: (1)..(1)
<223> OTHER INFORMATION: Xaa can be any naturally occurring amino acid

<400> SEQUENCE: 15
```

```
Xaa His Trp Ser His Gly Trp Tyr Pro Gly
 1               5                  10

<210> SEQ ID NO 16
<211> LENGTH: 10
<212> TYPE: PRT
<213> ORGANISM: Salmo sp.
<220> FEATURE:
<221> NAME/KEY: misc_feature
<222> LOCATION: (1)..(1)
<223> OTHER INFORMATION: Xaa can be any naturally occurring amino acid

<400> SEQUENCE: 16

Xaa His Trp Ser Tyr Gly Trp Leu Pro Gly
 1               5                  10

<210> SEQ ID NO 17
<211> LENGTH: 9
<212> TYPE: PRT
<213> ORGANISM: Artificial
<220> FEATURE:
<223> OTHER INFORMATION: a nonapeptide GnRH analog

<400> SEQUENCE: 17

Lys Trp Ser Tyr Gly Leu Arg Pro Gly
 1               5

<210> SEQ ID NO 18
<211> LENGTH: 10
<212> TYPE: PRT
<213> ORGANISM: Artificial
<220> FEATURE:
<223> OTHER INFORMATION: a decapeptide GnRH analog

<400> SEQUENCE: 18

Cys Lys Trp Ser Tyr Gly Leu Arg Pro Gly
 1               5                  10

<210> SEQ ID NO 19
<211> LENGTH: 20
<212> TYPE: PRT
<213> ORGANISM: Artificial
<220> FEATURE:
<223> OTHER INFORMATION: a dimer of a decapeptide GnRH analog

<400> SEQUENCE: 19

Gly Pro Arg Leu Gly Tyr Ser Trp Lys Cys Cys Lys Trp Ser Tyr Gly
 1               5                  10                  15

Leu Arg Pro Gly
            20

<210> SEQ ID NO 20
<211> LENGTH: 20
<212> TYPE: PRT
<213> ORGANISM: Artificial
<220> FEATURE:
<223> OTHER INFORMATION: a polymer of 2 GnRH decapeptides
<220> FEATURE:
<221> NAME/KEY: misc_feature
<222> LOCATION: (1)..(1)
<223> OTHER INFORMATION: Xaa can be any naturally occurring amino acid

<400> SEQUENCE: 20

Xaa His Trp Ser Tyr Gly Leu Arg Pro Gly Gln His Trp Ser Tyr Gly
 1               5                  10                  15

Leu Arg Pro Gly
```

```
<210> SEQ ID NO 21
<211> LENGTH: 21
<212> TYPE: PRT
<213> ORGANISM: Artificial
<220> FEATURE:
<223> OTHER INFORMATION: a GnRH analog
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 21

Xaa His Trp Ser Tyr Xaa Leu Arg Pro Gly Gln His Trp Ser Tyr Xaa
1               5                   10                  15

Leu Arg Pro Gly Cys
            20
```